US012357279B1

(12) United States Patent
Jiang et al.

(10) Patent No.: US 12,357,279 B1
(45) Date of Patent: Jul. 15, 2025

(54) SYSTEM AND METHOD FOR EXTRACTING A TWO-DIMENSIONAL SHORT AXIS VIEW OF A LEFT ATRIAL APPENDAGE

(71) Applicant: GE Precision Healthcare LLC, Waukesha, WI (US)

(72) Inventors: Hongjian Jiang, Jiangsu (CN); Olivier Gerard, Oslo (NO)

(73) Assignee: GE Precision Healthcare LLC, Waukesha, WI (US)

( * ) Notice: Subject to any disclaimer, the term of this patent is extended or adjusted under 35 U.S.C. 154(b) by 40 days.

(21) Appl. No.: 18/398,491

(22) Filed: Dec. 28, 2023

(51) Int. Cl.
*A61B 8/00* (2006.01)
*A61B 8/08* (2006.01)
*A61B 8/12* (2006.01)

(52) U.S. Cl.
CPC ............ *A61B 8/523* (2013.01); *A61B 8/0883* (2013.01); *A61B 8/465* (2013.01); *A61B 8/469* (2013.01); *A61B 8/483* (2013.01); *A61B 8/5207* (2013.01); *A61B 8/5223* (2013.01); *A61B 8/12* (2013.01)

(58) Field of Classification Search
CPC ....... A61B 8/523; A61B 8/0883; A61B 8/465; A61B 8/469; A61B 8/483; A61B 8/5207; A61B 8/5223; A61B 8/12
See application file for complete search history.

(56) References Cited

U.S. PATENT DOCUMENTS

| | | | |
|---|---|---|---|
| 11,534,136 B2 * | 12/2022 | Funka-Lea | A61B 8/5261 |
| 11,712,220 B2 | 8/2023 | Toporek et al. | |
| 12,154,273 B1 * | 11/2024 | Upadhyay | G06T 7/0012 |
| 2019/0090951 A1 * | 3/2019 | Camus | A61B 8/483 |
| 2021/0000446 A1 | 1/2021 | Toporek et al. | |
| 2021/0038321 A1 | 2/2021 | Toporek et al. | |
| 2022/0296306 A1 | 9/2022 | Camus et al. | |

OTHER PUBLICATIONS

Nucifora G et al. Evaluation of the left atrial appendage with real-time 3-dimensional transesophageal echocardiography: implications for catheter-based left atrial appendage closure. Circ Cardiovasc Imaging. Sep. 2011;4(5):514-23. doi: 10.1161/CIRCI.*

(Continued)

*Primary Examiner* — Bo Joseph Peng
(74) *Attorney, Agent, or Firm* — McAndrews, Held & Malloy, Ltd.; Daniel Bissing; David Bates

(57) ABSTRACT

Systems and methods for automatically acquiring an ultrasound volume to extract a two-dimensional short axis view of a left atrial appendage are provided. The method includes acquiring, by an ultrasound probe, a two-dimensional long axis ultrasound image view of a left atrial appendage. The method includes automatically detecting a first point on a circumflex artery side of the left atrial appendage and a second point on a left atrial ridge side of the left atrial appendage in the two-dimensional long axis ultrasound image view. The method includes acquiring, by the ultrasound probe, an ultrasound volume comprising the left atrial appendage. The method includes automatically extracting from the ultrasound volume an ultrasound image substantially in a plane extending through the first point and the second point. The method includes causing a display system to present the ultrasound image.

20 Claims, 10 Drawing Sheets

(56) References Cited

OTHER PUBLICATIONS

Patti G et al. Working Group of Thrombosis of the Italian Society of Cardiology. The left atrial appendage: from embryology to prevention of thromboembolism. Eur Heart J. Mar. 21, 2017;38(12):877-887. doi: 10.1093/eurheartj/ehw159. PMID: 27122600.*

Jiang C. et al. Comparison of left atrial and left atrial appendage mechanics in the risk stratification of stroke in patients with atrial fibrillation. Cardiovasc Ultrasound. Jan. 9, 2021;19(1):7. doi: 10.1186/s12947-020-00232-z. PMID: 33422087; PMCID: PMC7797160.*

Abdelmoneim SS, Mulvagh SL. Techniques To Improve Left Atrial Appendage Imaging. J Atr Fibrillation. Jun. 30, 2014;7(1):1059. doi: 10.4022/jafib.1059. PMID: 27957080; PMCID: PMC5135149.*

Rodés-Cabau J. et al. Safety and effects of volume loading during transesophageal echocardiography in the pre-procedural work-up for left atrial appendage closure. Cardiovasc Ultrasound. Jan. 2, 2021;19(1):3. doi: 10.1186/s12947-020-00230-1. PMID: 33388071; PMCID: PMC7778814.*

Beigel, R, Wunderlich, N, Ho, S. et al. The Left Atrial Appendage: Anatomy, Function, and Noninvasive Evaluation. J Am Coll Cardiol Img. Dec. 2014, 7 (12) 1251-1265. https://doi.org/10.1016/j.jcmg.2014.08.009.*

Xing Y. et al., Left Atrial Appendage Morphology and Local Thrombogenesis-Related Blood Parameters in Patients With Atrial Fibrillation. J Am Heart Assoc. Jun. 15, 2021;10(12):e020406. doi: 10.1161/JAHA.120.020406. Epub Jun. 5, 2021. PMID: 34096335; PMCID: PMC8477894.*

Zhu L. et al., A Comparative Study of Three Imaging Modalities for Size Selection of a Watchman Left Atrial Appendage Closure Device. Yonsei Med J. Apr. 2022;63(4):325-332. doi: 10.3349/ymj.2022.63.4.325. PMID: 35352883; PMCID: PMC8965429.*

GE Healthcare, "The Real Power of AI in Women's Health," Voluson Club, Europe-Middle East, https://www.volusonclub.net/emea/ai-innovations, 2024, 3 pages.

* cited by examiner

SYSTEM AND METHOD FOR EXTRACTING A TWO-DIMENSIONAL SHORT AXIS VIEW OF A LEFT ATRIAL APPENDAGE

FIELD

Certain embodiments relate to ultrasound imaging. More specifically, certain embodiments relate to a method and system for automatically acquiring an ultrasound volume to extract a two-dimensional (2D) short axis view of a left atrial appendage.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Atrial fibrillation is caused by a disturbance of electrical signals in muscles of the upper heart chambers. Blood flow to the body decreases when the heart pumps irregularly, as in the case of atrial fibrillation. The slow moving blood flow increases the likelihood of a blood clot, which can lead to a stroke. In many cases, the clots may form in the left atrial appendage, which is a small, pouch-like sac in the upper left chamber of the heart. The clot may cause a stroke if it travels through the arteries in the heart. Blood thinners are one form of treatment for atrial fibrillation. However, not all patients are able to take blood thinners. Another treatment is a left atrial appendage closure procedure (LAAC), which involves the insertion of an occlusion device using a catheter to close the left atrial appendage. There are a number of different types of occlusion devices. Measurements of the orifice area of the left atrial appendage shown in the 2D short axis view of the left atrial appendage may provide guidance for selecting an appropriate occlusion device.

The process of obtaining a two-dimensional (2D) short axis view to perform measurements of the orifice area of the left atrial appendage is a time consuming and labor intensive process for an ultrasound operator. For example, an ultrasound operator uses one hand to manipulate a Transesophageal Echocardiography (TEE) ultrasound probe to acquire a two-dimensional long axis view of the left atrial appendage. Next, the ultrasound operator may use their other hand to provide a number of selections, such as entering a four-dimensional (4D) preparation mode, moving a region of interest (ROI) box presented at a display system to cover the left atrial appendage, entering a 4D acquisition mode to acquire a 4D volume using the TEE probe, manipulating a trackball to rotate a viewing angle of the acquired ultrasound volume, entering a 2D slice viewing mode, setting the 2D slice viewing plane as the 2D short axis view, and performing the measurements of the orifice area of the left atrial appendage in the 2D short axis view. As shown above, the process for obtaining the 2D short axis view such that the orifice measurements of the left atrial appendage can be performed and the appropriate occlusion device can be selected is a time consuming and labor intensive process for the ultrasound operator.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically acquiring an ultrasound volume to extract a two-dimensional (2D) short axis view of a left atrial appendage, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
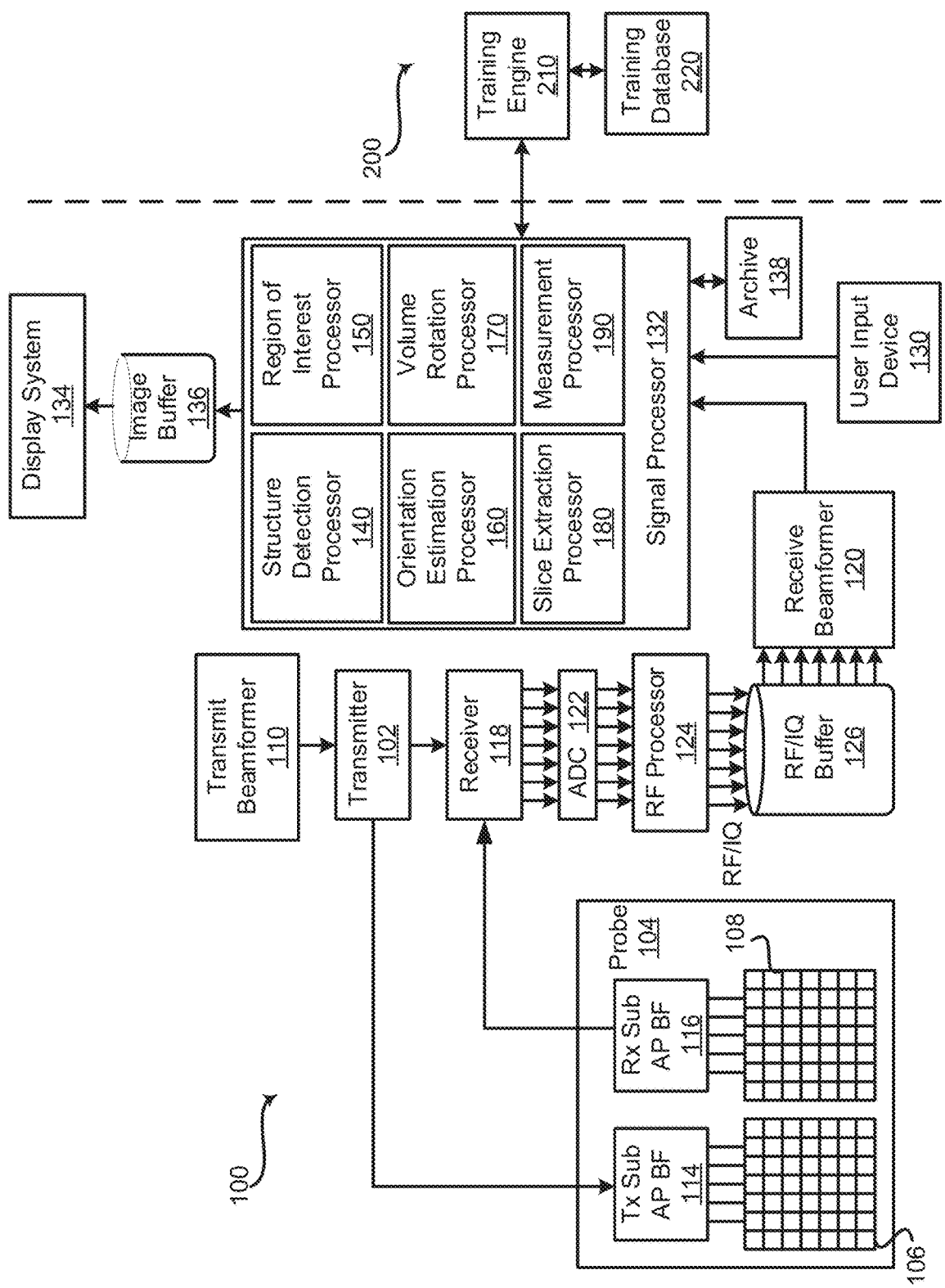
FIG. 1 is a block diagram of an exemplary ultrasound system that is operable to automatically acquire an ultrasound volume to extract a two-dimensional (2D) short axis view of a left atrial appendage, in accordance with various embodiments.

Certain embodiments may be found in a method and system for automatically acquiring an ultrasound volume to extract a two-dimensional (2D) short axis view of a left atrial appendage. Aspects of the present disclosure have the technical effect of automatically navigating from a 2D long axis view of a left atrial appendage to a 2D short axis view of the left atrial appendage in response to a single user input. Certain embodiments have the technical effect of automatically acquiring an ultrasound volume (e.g., 3D/4D) focused on a left atrial appendage. Aspects of the present disclosure provide the technical effect of automatically rotating an ultrasound volume (e.g., 3D/4D) to a pre-defined orientation associated with the left atrial appendage. Various embodiments have the technical effect of automatically navigating from a 2D long axis view to a 2D short axis view and automatically performing at least one measurement of an orifice area of a left atrial appendage in response to a single user input.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode or 2D mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-Flow Color (BFC), Micro Vascular Imaging (MVI), Ultrasound-Guided Attenuation Parameter (UGAP), and the like, such as where the "image" and/or "plane" includes a single beam or multiple beams.

Furthermore, the term processor or processing unit, as used herein, refers to any type of processing unit that can carry out the required calculations needed for the various embodiments, such as single or multi-core Central Processing Unit (CPU), Accelerated Processing Unit (APU), Graphic Processing Unit (GPU), Digital Signal Processor (DSP), Field Programmable Gate Array (FPGA), System on a Chip (SoC), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically acquire an ultrasound volume to extract a two-dimensional (2D) short axis view of a left atrial appendage, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements. Additionally and/or alternatively, the ultrasound probe 104 may be a mechanically wobbling ultrasound probe 104, which may comprise a one dimensional (1D) array of piezoelectric elements mounted on a transducer assembly movable in a single plane. For example, the transducer assembly may be movable approximately 120 to 150 degrees by a motor driving gears, belts, and/or rope to pivot an axis or hub of the transducer assembly. In certain embodiments, the ultrasound probe 104 is a Transesophageal Echocardiography (TEE) ultrasound probe. The ultrasound probe 104 may comprise a group of transmit transducer elements 106 and a group of receive transducer elements 108, that normally constitute the same elements. The group of transmit transducer elements 106 may emit ultrasonic signals through oil and a probe cap and into a target. In a representative embodiment, the ultrasound probe 104 may be operable to acquire ultrasound image data covering at least a substantial portion of an anatomy, such as a heart or any suitable anatomical structure. In an exemplary embodiment, the ultrasound probe 104 may be operated in a volume acquisition mode, where the transducer assembly of the ultrasound probe 104 acquires a plurality of parallel 2D ultrasound slices forming an ultrasound volume.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, initiate volume acquisition and two-dimensional (2D) short axis view plane extraction, modify a region of interest, and the like. In an exemplary embodiment, the user input device 130 may be operable to configure, manage and/or control operation of one or more components, modules, and/or devices in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a structure detection processor 140, a region of interest processor 150, an orientation estimation processor 160, a volume rotation processor 170, a slice extraction processor 180, and a measurement processor 190. The signal processor 132 may be capable of receiving input information from a user input device 130 and/or archive 138, generating an output displayable by a display system 134, and manipulating the output in response to input information from a user input device 130, among other things. The signal processor 132, structure detection processor 140, region of interest processor 150, orientation estimation processor 160, volume rotation processor 170, slice extraction processor, and measurement processor 190 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

Figure 2:
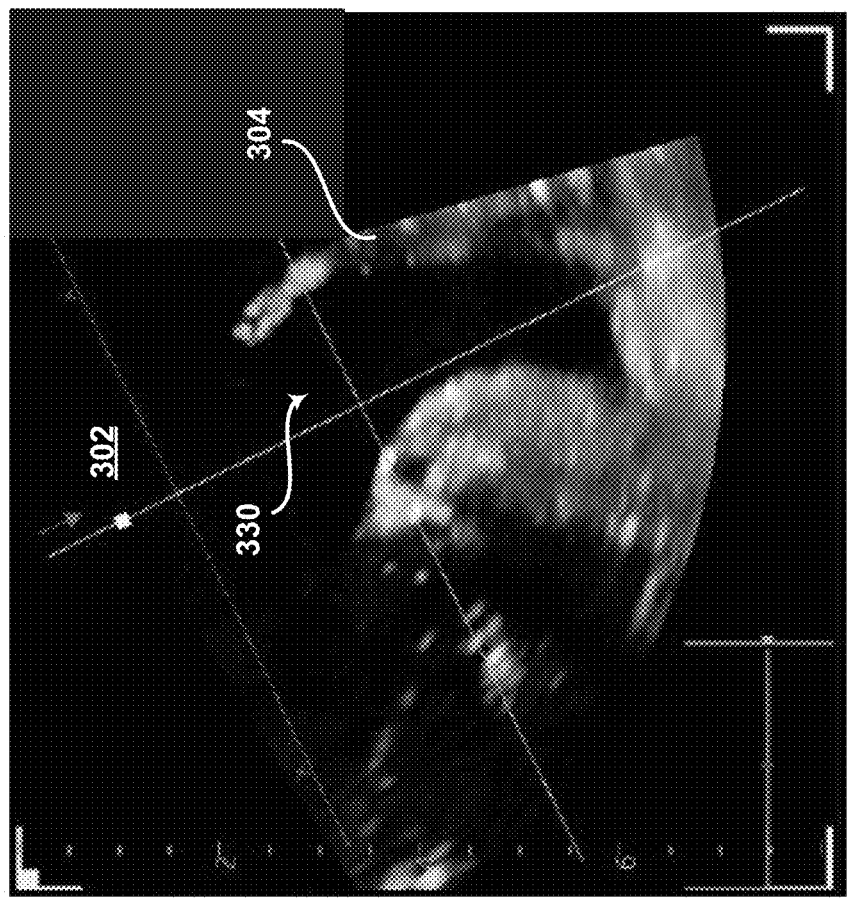
FIG. 2 is an exemplary display of a two-dimensional (2D) long axis ultrasound image view of a left atrial appendage, in accordance with various embodiments.

In an exemplary embodiment, an ultrasound operator preparing for a left atrial appendage closure procedure (LAAC), for example, may manipulate the ultrasound probe 104 to acquire two-dimensional (2D) long axis view (LAX) ultrasound images of a left atrial appendage. The 2D LAX view may be a starting point for navigating to a 2D short axis view (SAX), which includes a view of the orifice of the left atrial appendage that is measured to select an appropriate occlusion device for the LAAC procedure. FIG. 2 is an exemplary display 300 of a two-dimensional (2D) long axis ultrasound image view 304 of a left atrial appendage 330, in accordance with various embodiments. Referring to FIG. 2, a screenshot 300, which may be provided at a display system 134 of the ultrasound system 100 of FIG. 1, includes an image display portion 302 having an ultrasound image 304. The ultrasound image 304 shown in FIG. 2 is a 2D LAX ultrasound image view of a left atrial appendage 330.

The signal processor 132 may include a structure detection processor 140 that comprises suitable logic, circuitry, interfaces and/or code that may be operable to analyze acquired two-dimensional (2D) long axis view (LAX) ultrasound images of a left atrial appendage as shown in FIG. 2 and/or ultrasound volumes of a region of interest surrounding a left atrial appendage to detect a presence and location of anatomical structures, such as a first point on a circumflex artery side of the left atrial appendage and a second point on a left atrial ridge side of the left atrial appendage. In this regard, the structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize anatomical structures in ultrasound images and/or volumes. Additionally and/or alternatively, the image analysis techniques, artificial intelligence, or machine learning processing functionality configured to detect and localize anatomical structures in ultrasound images and/or volumes may be provided by a different processor or distributed across multiple processors at the ultrasound system 100 and/or a remote processor communicatively coupled to the ultrasound system 100. For example, the structure detection and localization functionality may be provided as a deep neural network that may be made up of, for example, an input layer, an output layer, and one or more hidden layers in between the input and output layers. Each of the layers may be made up of a plurality of processing nodes that may be referred to as neurons. For example, the structure detection and localization functionality may include an input layer having a neuron for each pixel of an ultrasound image and/or voxel of an ultrasound volume. The output layer may have a neuron corresponding to each heart muscle, heart chamber, and/or any suitable anatomical structure. Each neuron of each layer may perform a processing function and pass the processed ultrasound image information to one of a plurality of neurons of a downstream layer for further processing. As an example, neurons of a first layer may learn to recognize edges of structure in the obtained ultrasound image and/or volume. The neurons of a second layer may learn to recognize shapes based on the detected edges from the first layer. The neurons of a third layer may learn positions of the recognized shapes relative to landmarks in the obtained ultrasound image and/or volume. The processing performed by the deep neural network may identify anatomical structures and the location of the anatomical structures in the obtained ultrasound images and/or volume with a high degree of probability.

In an exemplary embodiment, the structure detection processor 140 may be configured to analyze the ultrasound images and/or volume to detect and localize a first point on a circumflex artery side of the left atrial appendage and a second point on a left atrial ridge side of the left atrial appendage. For example, once the ultrasound operator acquires the 2D LAX view of the left atrial appendage, the ultrasound operator may provide a user input to initiate the acquisition of an ultrasound volume and the extraction of a 2D SAX view of the left atrial appendage for measurement. The structure detection processor 140 may be configured to analyze the 2D LAX ultrasound image to detect and localize a first point on a circumflex artery side of the left atrial appendage and a second point on a left atrial ridge side of the left atrial appendage in response to receiving the user input. The structure detection processor 140 may be configured to analyze a subsequently acquired ultrasound volume to continue detecting and tracking the first point on the circumflex artery side of the left atrial appendage and the second point on the left atrial ridge side of the left atrial appendage in the ultrasound volume.

Figure 3:
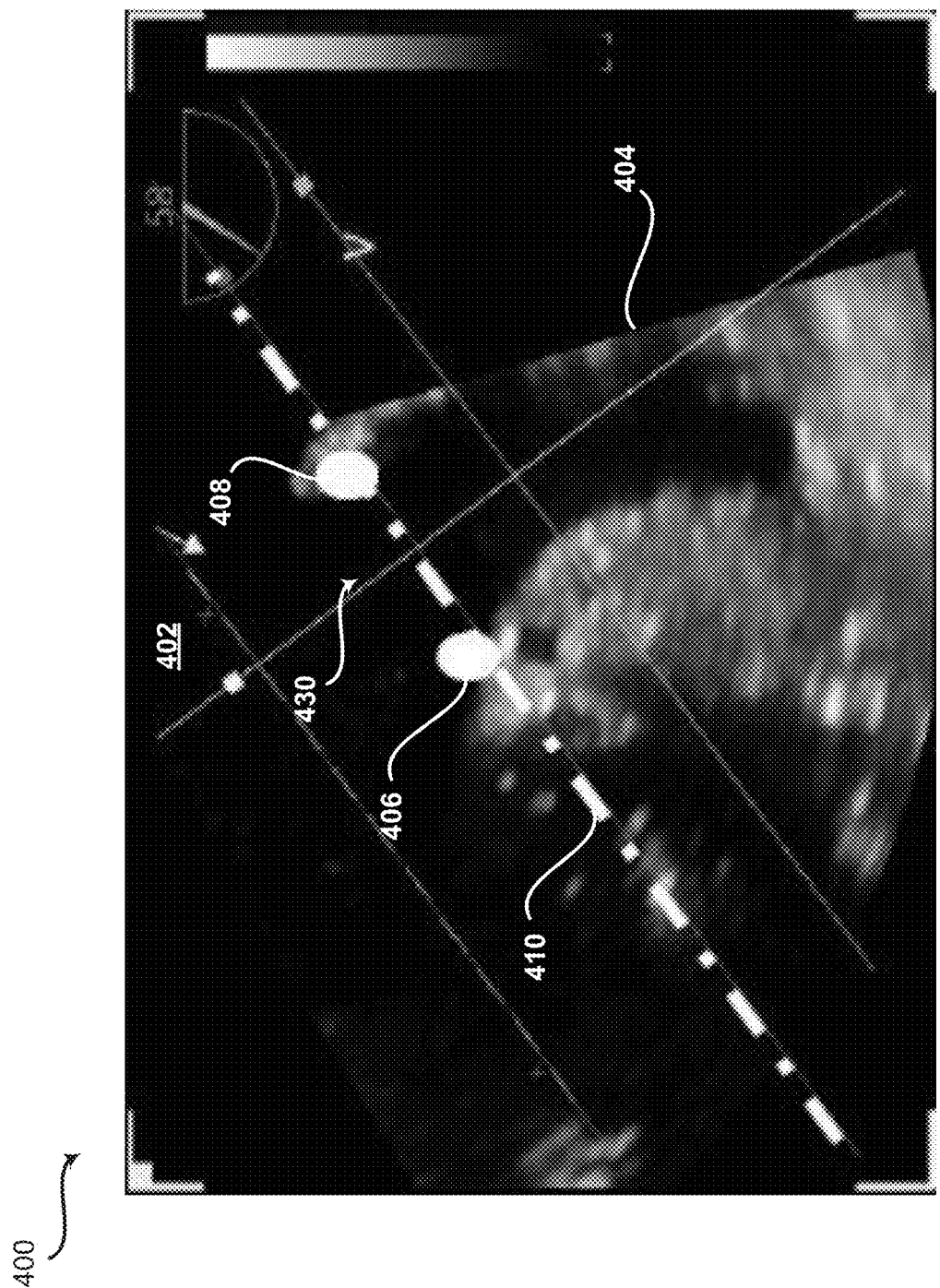
FIG. 3 is an exemplary display of a two-dimensional (2D) long axis ultrasound image view of a left atrial appendage having an automatically detected first point on a circumflex artery side of the left atrial appendage and an automatically detected second point on a left atrial ridge side of the left atrial appendage, in accordance with various embodiments.

FIG. 3 is an exemplary display 400 of a two-dimensional (2D) long axis ultrasound image view 404 of a left atrial appendage 430 having an automatically detected first point 406 on a circumflex artery side of the left atrial appendage 430 and an automatically detected second point 408 on a left atrial ridge side of the left atrial appendage 430, in accordance with various embodiments. Referring to FIG. 3, a screenshot 400, which may be provided at a display system 134 of the ultrasound system 100 of FIG. 1, includes an image display portion 402 having an ultrasound image 404. The ultrasound image 404 shown in FIG. 3 is a 2D LAX ultrasound image view of a left atrial appendage 430. The structure detection processor 140 may be configured to analyze the 2D LAX ultrasound image 404 to detect and track the first point 406 on the circumflex artery side of the left atrial appendage 430 and the second point 408 on the left atrial ridge side of the left atrial appendage 430. In various embodiments, the structure detection processor 140 may be configured to identify a plane 410 extending through the first point 406 and second point 408, which corresponds with a 2D SAX ultrasound image view of the left atrial appendage 430. The detected and localized first point 406, second point 408, identified plane 410, and/or left atrial appendage 430 may be provided by the structure detection processor 140 to the region of interest processor 150 and/or the slice extraction processor 180. Additionally and/or alternatively, the detected and localized first point 406, second point 408, identified plane 410, and/or left atrial appendage 430 may be stored at archive 138 and/or any suitable computer readable medium.

Referring again to FIG. 1, the signal processor 132 may include a region of interest processor 150 that comprises suitable logic, circuitry, interfaces and/or code that may be operable to automatically position a region of interest surrounding the left atrial appendage detected and localized by the structure detection processor 140. For example, the region of interest processor 150 may be configured to receive from the structure detection processor 140, or retrieve from the archive 138 and/or any suitable data storage medium, the location of the first point 406, second point 408, and/or left atrial appendage 430. The region of interest processor 150 may be configured to position the region of interest to surround the first point 406, second point 408, and/or left atrial appendage 430. The region of interest defines the location at which an ultrasound volume is acquired. In various embodiments, the region of interest processor 150 may optionally present the positioned region of interest at the display system 134 by overlaying a bounding box, colorizing pixels, and/or any suitable identification technique. The region of interest processor 150 may comprise suitable logic, circuitry, interfaces, and/or code that may be operable to initiate a 3D/4D volume acquisition by the ultrasound probe 104 focused/zoomed on the region of interest after positioning the region of interest to surround the left atrial appendage 430.

Figure 4:
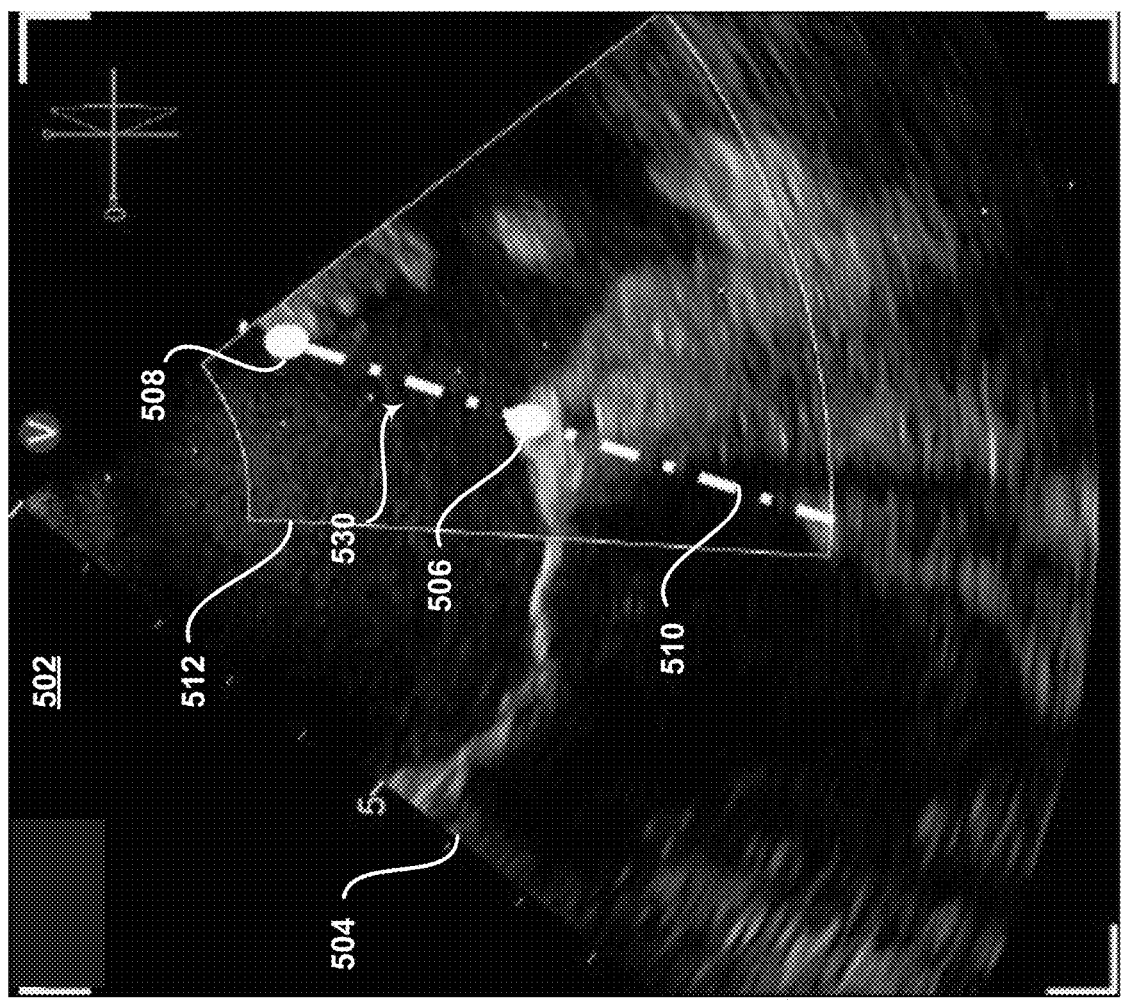
FIG. 4 is an exemplary display of a two-dimensional (2D) long axis ultrasound image view of a left atrial appendage having an automatically positioned region of interest surrounding the automatically detected left atrial appendage, in accordance with various embodiments.

FIG. 4 is an exemplary display 500 of a two-dimensional (2D) long axis ultrasound image view 504 of a left atrial appendage 530 having an automatically positioned region of interest 512 surrounding the automatically detected left atrial appendage 530, in accordance with various embodiments. Referring to FIG. 4, a screenshot 500, which may be provided at a display system 134 of the ultrasound system 100 of FIG. 1, includes an image display portion 502 having an ultrasound image 504. The ultrasound image 504 shown in FIG. 4 is a 2D LAX ultrasound image view of a left atrial appendage 530. The structure detection processor 140 may be configured to analyze the 2D LAX ultrasound image 504 to detect and track the first point 506 on the circumflex artery side of the left atrial appendage 530 and the second point 508 on the left atrial ridge side of the left atrial appendage 530. In various embodiments, the structure detection processor 140 may be configured to identify a plane 510 extending through the first point 506 and second point 508, which corresponds with a 2D SAX ultrasound image view of the left atrial appendage 530. The detected and localized first point 506, second point 508, and/or left atrial appendage 530 may be provided by the structure detection processor 140 to the region of interest processor 150 and/or stored at archive 138 and/or any suitable computer readable medium for retrieval by the region of interest processor 150. The region of interest processor 150 may be configured to automatically position a region of interest 512 surrounding the left atrial appendage 530. In various embodiments, the region of interest processor 150 may be configured to present the region of interest positioned to surround the left atrial appendage 530 at the display system 134. The region of interest processor 150 may be configured to automatically initiate a 3D/4D volume acquisition by the ultrasound probe 104 focused/zoomed on the region of interest 512.

Referring again to FIG. 1, in certain embodiments, the region of interest processor 150 may comprise suitable logic, circuitry, interfaces, and/or code that may be operable to modify the region of interest in response to a user input. For example, in embodiments where the region of interest processor 150 causes the display system 134 to present the region of interest 512 surrounding the left atrial appendage 530, an ultrasound operator may provide an input via the user input device 130 and/or touchscreen display 130, 134 to modify a size and/or location of the displayed region of interest. The region of interest processor 150 may be configured to initiate a 3D/4D volume acquisition of the region of interest 512 automatically and/or in response to a user input. For example, the region of interest processor 150 may automatically initiate the 3D/4D volume acquisition by the ultrasound probe 104 if a user input is not received to modify the position and/or size of the region of interest 512 in a predetermined period of time. As another example, the region of interest processor 150 may be configured to initiate the 3D/4D volume acquisition by the ultrasound probe 104 in response to a user input. In addition, the region of interest processor 150 may be configured to initiate the 3D/4D volume acquisition by the ultrasound probe 104 in response to a predetermined period of time expiring after the region of interest 512 has been modified and/or in response to a user input after the region of interest 512 has been modified. Alternatively, in a representative embodiment, the region of interest 512 may not be displayed and/or may not be modifiable.

The signal processor 132 may include an orientation estimation processor 160 that comprises suitable logic, circuitry, interfaces and/or code that may be operable to estimate a current orientation of the left atrial appendage within the 2D LAX ultrasound image 504 and/or an acquired 3D/4D volume of the region of interest 512. For example, the orientation estimation processor 160 may perform image segmentation and/or any suitable image identification techniques to estimate a current orientation of the left atrial appendage depicted in the 2D LAX ultrasound image 504 and/or the acquired ultrasound volume. The orientation estimation processor 160 may be configured to segment and/or otherwise identify the left atrial appendage within the image data. In this regard, the orientation estimation processor 160 may include, for example, image analysis algorithms, artificial intelligence algorithms, one or more deep neural networks (e.g., a convolutional neural network such as u-net) and/or may utilize any suitable form of artificial intelligence image analysis techniques or machine learning processing functionality configured to provide segmentation of the left atrial appendage and/or any suitable anatomical structure. Additionally and/or alternatively, the image analysis techniques, artificial intelligence algorithms, or machine learning processing functionality configured to segment the left atrial appendage in the image data may be provided by a different processor or distributed across multiple processors at the ultrasound system 100 and/or a remote processor communicatively coupled to the ultrasound system 100. For example, the image segmentation/identification functionality may be provided as a deep neural network that may be made up of, for example, an input layer, an output layer, and one or more hidden layers in between the input and output layers. Each of the layers may be made up of a plurality of processing nodes that may be referred to as neurons. For example, the image segmentation/identification functionality may include an input layer having a neuron for each pixel or voxel of the image data. The output layer may have a neuron corresponding to the left atrial appendage and/or any suitable anatomical structure. Each neuron of each layer may perform a processing function and pass the processed ultrasound image information to one of a plurality of neurons of a downstream layer for further processing. As an example, neurons of a first layer may learn to recognize edges of the left atrial appendage in the image data. The neurons of a second layer may learn to recognize shapes based on the detected edges from the first layer. The neurons of a third layer may learn positions of the recognized shapes relative to landmarks in the obtained ultrasound volume. The neurons of a fourth layer may learn to determine a major axis and/or minor axis from a shape of the left atrial appendage. The processing performed by the deep neural network may identify the left atrial appendage, the location of the left atrial appendage, and the estimated current orientation of the left atrial appendage in the image data with a high degree of probability.

In an exemplary embodiment, the orientation estimation processor 160 may be configured to store the estimated current orientation information at archive 138 and/or any suitable storage medium. The orientation estimation processor 160 may be configured to provide the volume rotation processor 170 with the estimated current orientation information. The estimated current orientation information may comprise, for example, location and boundaries of the left atrial appendage, shape of left atrial appendage, major/minor axis information, and the like.

Figure 5:
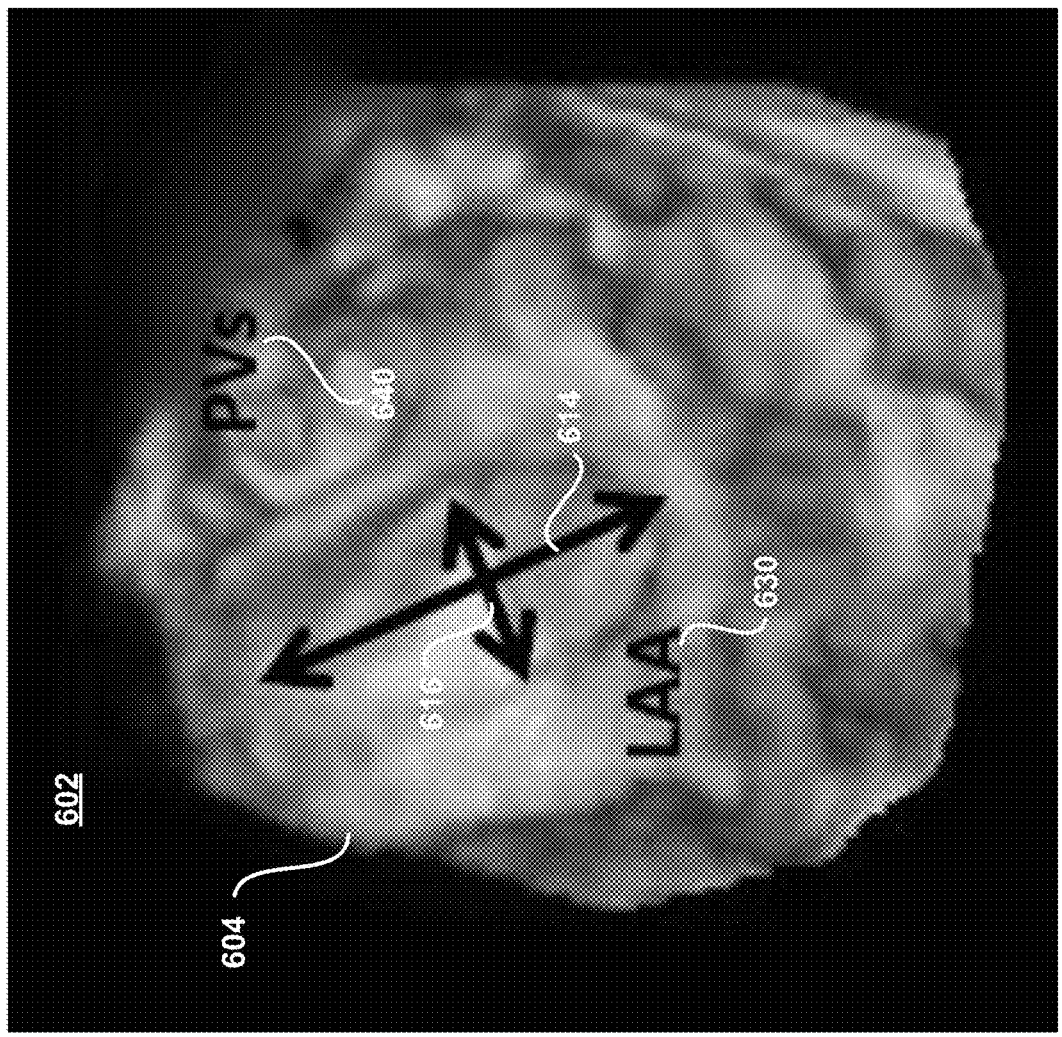
FIG. 5 is an exemplary display of a rendering of an acquired volume of the left atrial appendage prior to automatic rotation of the volume to a pre-defined orientation, in accordance with various embodiments.

FIG. 5 is an exemplary display 600 of a rendering of an acquired volume 604 of the left atrial appendage 630 prior to automatic rotation of the volume 604 to a pre-defined orientation, in accordance with various embodiments. Referring to FIG. 5, the display 600 comprises an image display portion 602 comprising a rendered ultrasound volume 604 of the region of interest (e.g., 512 from FIG. 4) surrounding the left atrial appendage 630. The rendered ultrasound volume 604 of the region of interest includes the left atrial appendage 630 and surrounding structures, such as pulmonary valves (PVs) 640. The left atrial appendage 630 comprises a shape having a major axis 614 and minor axis 616, which may be used by a volume rotation processor 170, along with the locations of surrounding anatomical structures 640, to rotate the ultrasound volume 604 to a pre-defined orientation. In various embodiments, the ultrasound volume 604 (i.e., prior to rotation) may not be displayed.

Referring again to FIG. 1, the signal processor 132 may include a volume rotation processor 170 that comprises suitable logic, circuitry, interfaces and/or code that may be operable to rotate the ultrasound volume 604 to a pre-defined orientation, render the rotated ultrasound volume, and cause a display system 134 to present the rotated and rendered ultrasound volume. For example, the volume rotation processor 170 may configured to rotate the ultrasound volume 604 based on the estimated current orientation information from the orientation estimation processor 160 and a pre-defined orientation. The pre-defined orientation may correspond with a standard orientation from echocardiography guidelines and/or any suitable pre-defined orientations from other guidelines, settings, and/or configurations. The volume rotation processor 170 may, for example, calculate a rotation angle and rotation amount to transform the volume from the estimated current orientation to the pre-defined orientation. The volume rotation processor 170 may reference the major axis 614 and/or minor axis 616 of the shape of 640 left atrial appendage 630 and the location information for the surrounding structure 640 in the estimated current orientation with reference to the pre-defined orientation information to calculate and provide the rotation amount and rotation angle to transform the ultrasound volume to the pre-defined orientation. The volume rotation processor 170 may be configured to render and cause a display system 134 to present the rotated and rendered ultrasound volume.

Figure 6:
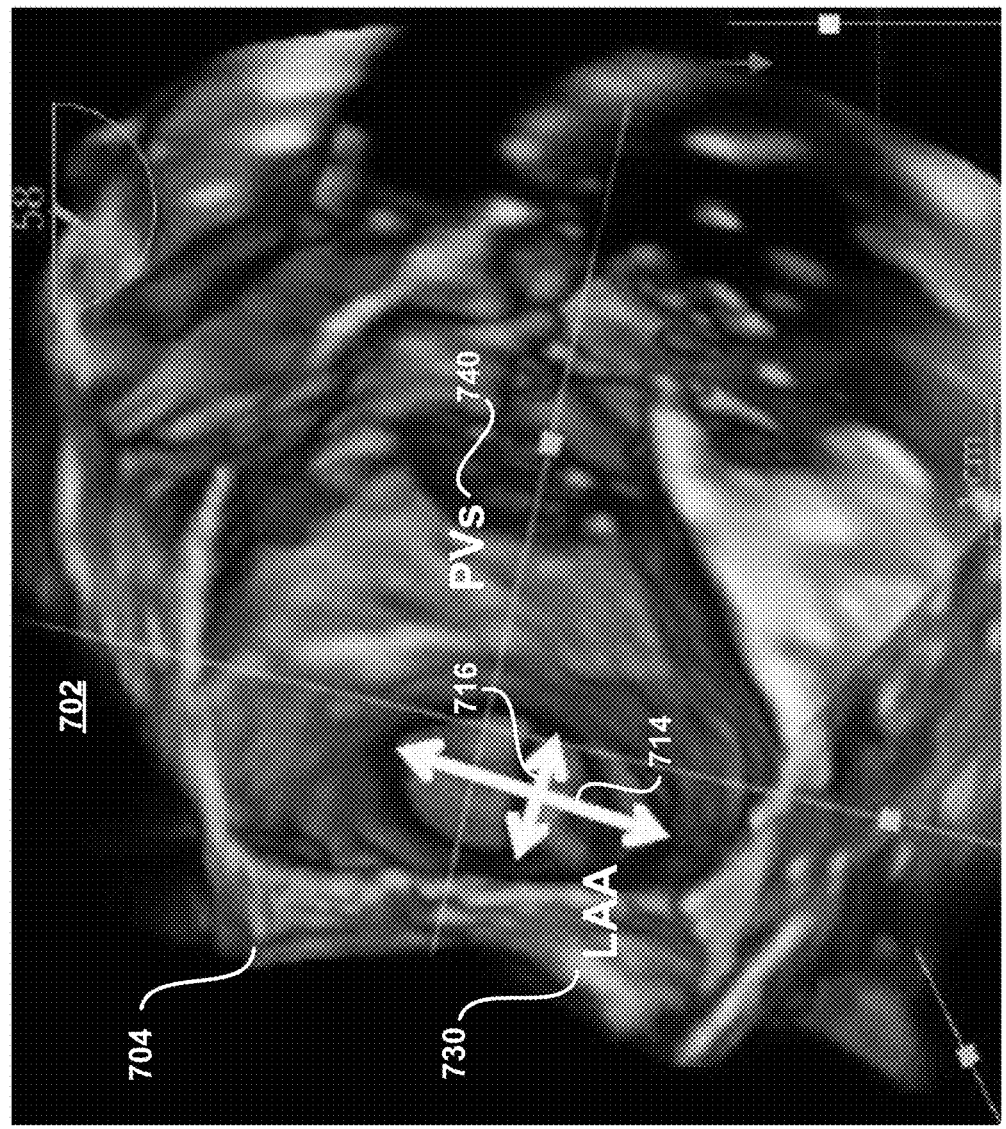
FIG. 6 is an exemplary display of a rendering of an acquired volume of the left atrial appendage after automatic rotation of the volume to a pre-defined orientation, in accordance with various embodiments.

FIG. 6 is an exemplary display 700 of a rendering of an acquired volume 704 of the left atrial appendage 730 after automatic rotation of the volume 704 to a pre-defined orientation, in accordance with various embodiments. Referring to FIG. 6, the display 700 comprises an image display portion 702 comprising a rotated (e.g., from 604 in FIG. 5) and rendered ultrasound volume 704 of the region of interest (e.g., 512 from FIG. 4) surrounding the left atrial appendage 730. The rotated and rendered ultrasound volume 704 of the region of interest includes the left atrial appendage 730 and surrounding structures, such as pulmonary valves (PVs) 740. The left atrial appendage 730 comprises a shape having a major axis 714 and minor axis 716, rotated by the volume rotation processor 170 from the major axis 614 and minor axis 616 of the volume at the estimated orientation 604. In various embodiments, the major axis 714 and minor axis 716 may not be displayed.

Referring again to FIG. 1, the signal processor 132 may include a slice extraction processor 180 that comprises suitable logic, circuitry, interfaces and/or code that may be operable to automatically extract and cause the display system 134 to present substantially the plane 510 extending through the first point 506 on the circumflex artery side of the left atrial appendage 530 and the second point 508 on the left atrial ridge side of the left atrial appendage 530. For example, the structure detection processor 140 may be configured to detect and track the first point 506 on the circumflex artery side of the left atrial appendage 530 and the second point 508 on the left atrial ridge side of the left atrial appendage 530 in the acquired ultrasound volume 604, 704. The structure detection processor 140 may be configured to identify a plane 510 extending through the first point 506 and second point 508. The slice extraction processor 180 may be configured to receive from the structure detection processor 140 or retrieve from archive 138 and/or any suitable data storage medium the locations of the first point 506, second point 508, and/or plane 510 identified by the structure detection processor 140. The slice extraction processor 180 may be configured to automatically extract and cause the display system 134 to present an ultrasound image substantially in the plane 510, which corresponds with a 2D SAX ultrasound image view of the left atrial appendage 530, based on the first point 506, second point 508, and/or plane 510 identified by the structure detection processor 140. For purposes of the present application, an ultrasound image "substantially" in the plane 510 refers to an ultrasound image of the plane 510 extending between the first 506 and second 508 points and/or an ultrasound image in planes parallel to plane 510 up to 1 centimeter into the left atrial appendage. In various embodiments, the slice extraction processor 180 is configured to extract and display additional planes selected by an ultrasound operator. For example, an ultrasound operator may position additional planes in the 2D LAX ultrasound view 504 and the slice extraction processor 180 may be configured to extract and display the additional planes corresponding with the locations selected by the ultrasound operator in the 2D LAX ultrasound view 504.

Figure 7:
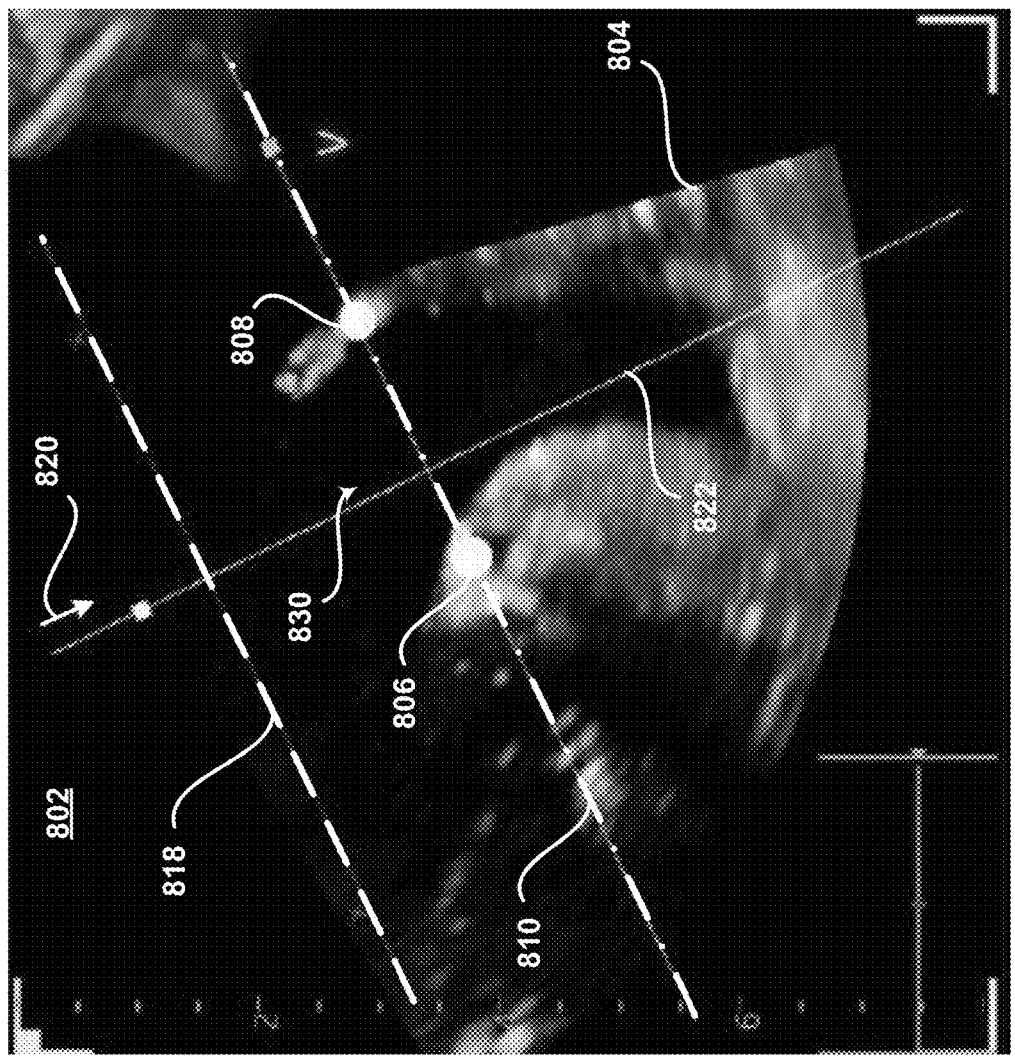
FIG. 7 is an exemplary display of a two-dimensional (2D) long axis ultrasound image view of a left atrial appendage having a cropping plane and viewing direction for a volume rendering of the left atrial appendage, and planes for the extraction of additional two-dimensional (2D) ultrasound image views of the left atrial appendage, in accordance with various embodiments.

FIG. 7 is an exemplary display 800 of a two-dimensional (2D) long axis ultrasound image view 804 of a left atrial appendage 830 having a cropping plane 818 and viewing direction 820 for a volume rendering 604, 704 of the left atrial appendage 830, and planes 810, 822 for the extraction of additional two-dimensional (2D) ultrasound image views of the left atrial appendage 830, in accordance with various embodiments. Referring to FIG. 7, a screenshot 800, which may be provided at a display system 134 of the ultrasound system 100 of FIG. 1, includes an image display portion 802 having an ultrasound image 804. The ultrasound image 804 shown in FIG. 7 is a 2D LAX ultrasound image view of a left atrial appendage 830. The structure detection processor 140 may be configured to analyze the 2D LAX ultrasound image 804 to detect and track the first point 806 on the circumflex artery side of the left atrial appendage 830 and the second point 808 on the left atrial ridge side of the left atrial appendage 830. In various embodiments, the structure detection processor 140 may be configured to identify a plane 810 extending through the first point 806 and second point 808, which corresponds with a 2D SAX ultrasound image view of the left atrial appendage 830. The detected and localized first point 806, second point 808, identified plane 810, and/or left atrial appendage 830 may be provided by the structure detection processor 140 to the region of interest processor 150 and/or the slice extraction processor 180. Additionally and/or alternatively, the detected and localized first point 806, second point 808, identified plane 810, and/or left atrial appendage 830 may be stored at archive 138 and/or any suitable computer readable medium. The display portion 802 may further comprise a cropping plane 818 and viewing direction 820 of the ultrasound volume 604, 704 that is rendered and presented at the display system 134. The display portion 802 further comprises an additional plane 822 selected by an ultrasound operator. In various embodiments, an ultrasound operator may select additional planes and/or modify the positions of planes 810, 822 to control the extraction and presentation of the slices presented at the display system 134. In an exemplary embodiment, an ultrasound operator may select and/or modify the position of cropping plane 818 and the viewing direction 820 to control the display of the rendered ultrasound volume 604, 704.

Figure 9:
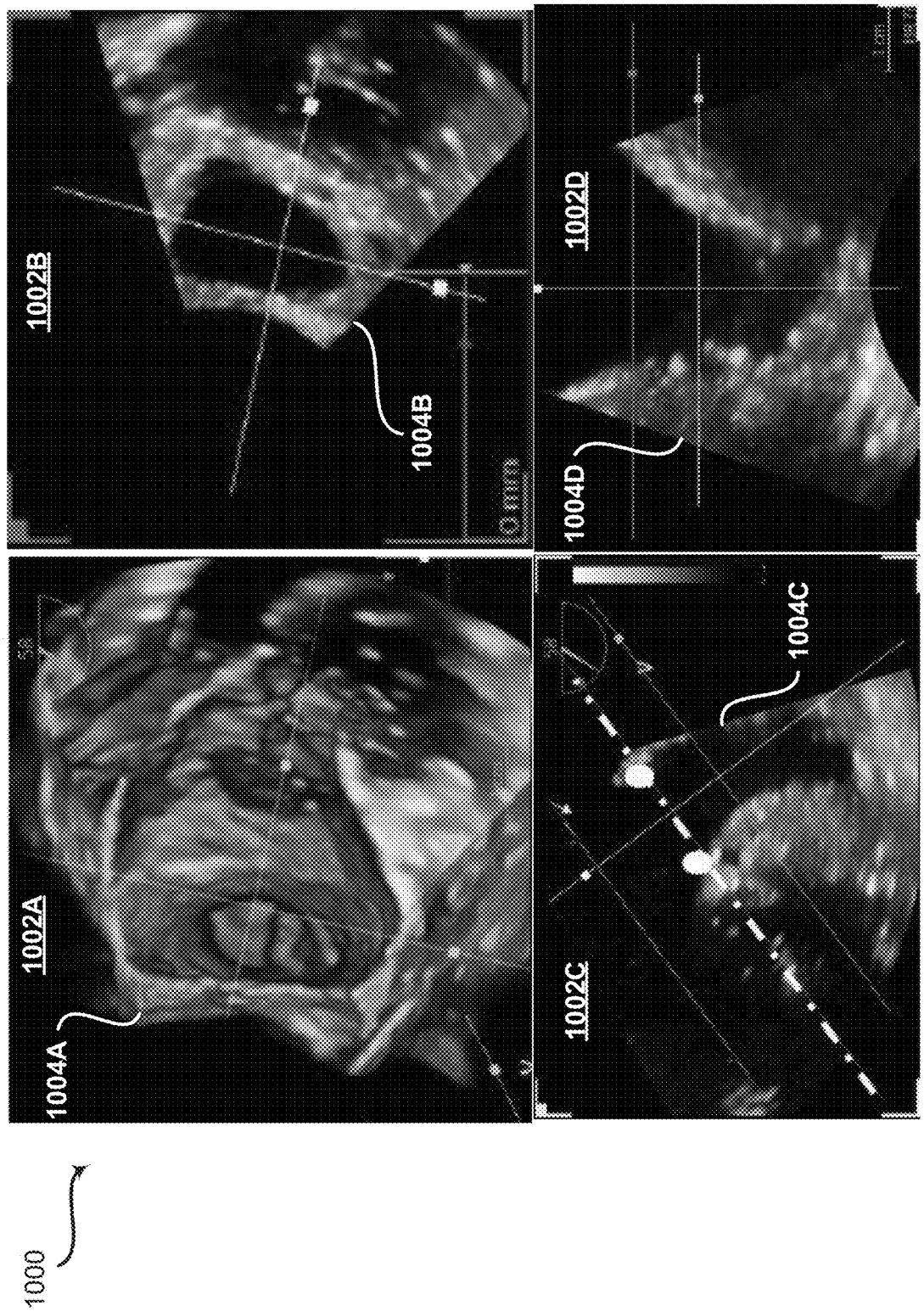
FIG. 9 is an exemplary display of a volume rendering and three (3), two-dimensional (2D) ultrasound image views of a left atrial appendage as identified by FIG. 7, in accordance with various embodiments.

FIG. 9 is an exemplary display 1000 of a volume rendering 1004A and three (3), two-dimensional (2D) ultrasound image views 1004B, 1004C, 1004D of a left atrial appendage as identified by FIG. 7, in accordance with various embodiments. Referring to FIG. 9, a screenshot 1000, which may be provided at a display system 134 of the ultrasound system 100 of FIG. 1, includes multiple image display portions 1002A, 1002B, 1002C, 1002D for presenting a volume rendering 1004A and 2D ultrasound image views 1004B, 1004C, 1004D extracted from the acquired 3D/4D ultrasound volume. The image display portion 1002C may share various characteristics with the image display portion 802 of FIG. 7. Referring to FIGS. 7 and 9, the image display portion 1002A of the volume rendering 1004A may be defined by the cropping plane 818, viewing direction 820, and the pre-defined orientation applied by the volume rotation processor 170. The image display portion 1002B presents the ultrasound image plane 1004B corresponding with the plane 810 through the first 806 and second 808 points of the left atrial appendage 830 as shown in FIG. 7 (i.e., the 2D SAX ultrasound image view). The image display portion 1002C presents the 2D LAX ultrasound image view corresponding with the 2D LAX ultrasound image view 804 of FIG. 7. The image display portion 1002D presents an additional ultrasound image plane 1004D corresponding with the additional ultrasound image plane 822 identified in FIG. 7. As shown in FIG. 9, the display system 134 may be configured to simultaneously present multiple ultrasound image views 1004A, 1004B, 1004C, 1004D in multiple image display portions 1002A, 1002B, 1002C, 1002D. In various embodiments, the multiple image display portions 1002A, 1002B, 1002C, 1002D may include more or less image display portions, may be arranged in a pre-defined or user selected manner, and/or may be provided on one or more display screens of the display system 134.

Referring again to FIG. 1, the signal processor 132 may include a measurement processor 190 that comprises suitable logic, circuitry, interfaces and/or code that may be operable to perform measurements of the orifice of the left atrial appendage depicted in the 2D SAX ultrasound view 1004B of the left atrial appendage. For example, the measurement processor 190 may be configured to perform circumference measurements, length measurements, width measurements, and/or any suitable measurements on the left atrial appendage orifice depicted in the 2D SAX ultrasound view 1004B. The measurement processor 190 may be configured to cause the display system 134 to present the measurement(s). The measurement processor 190 may be configured to store the measurement(s) at archive 138 and/or any suitable data storage medium.

Figure 8:
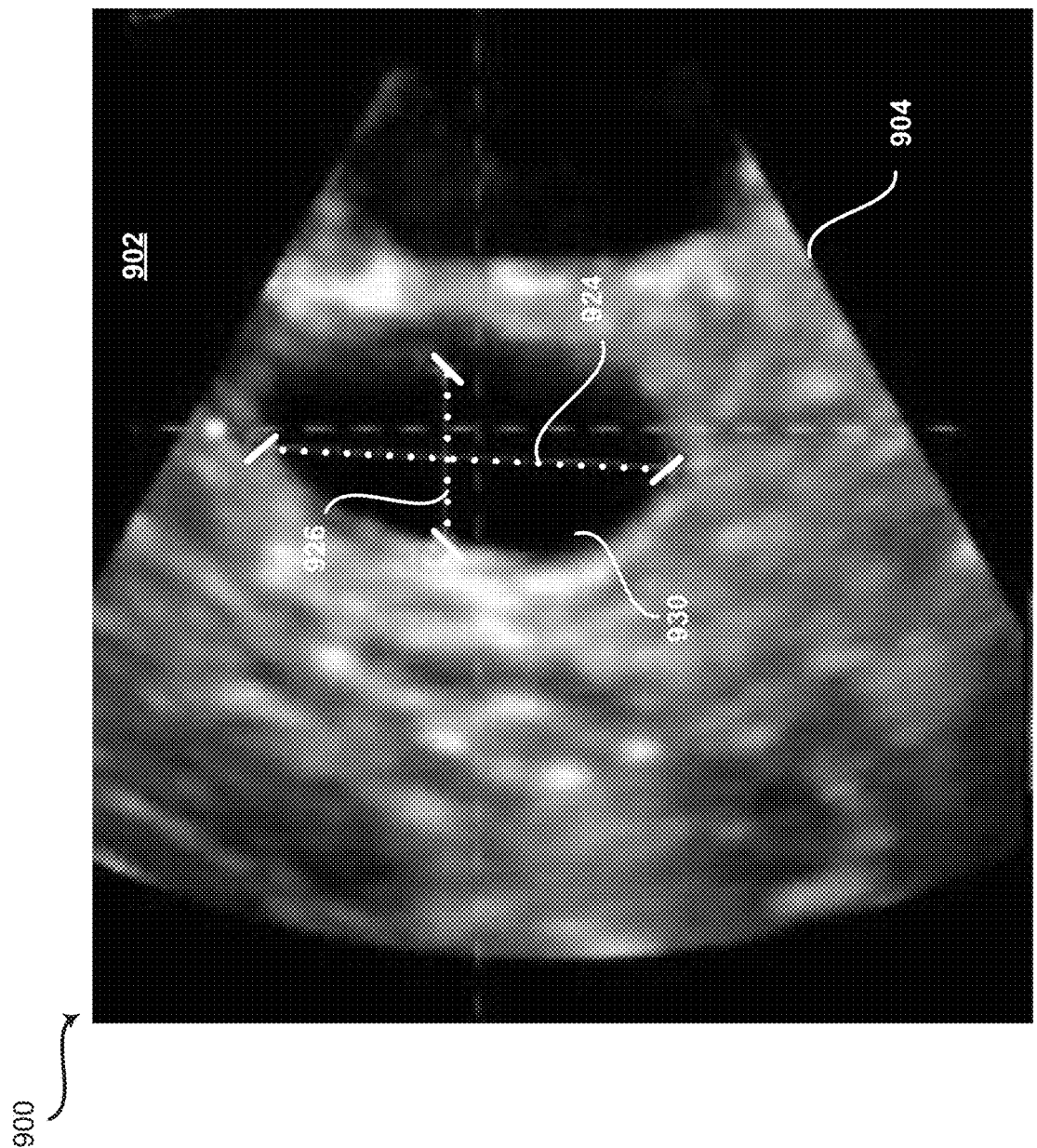
FIG. 8 is an exemplary display of a two-dimensional (2D) short axis ultrasound image view of the left atrial appendage having length and width measurements of an orifice of the left atrial appendage, in accordance with various embodiments.

FIG. 8 is an exemplary display 900 of a two-dimensional (2D) short axis ultrasound image view 904 of the left atrial appendage 930 having length 924 and width 926 measurements of an orifice of the left atrial appendage 930, in accordance with various embodiments. Referring to FIG. 8, a screenshot 900, which may be provided at a display system 134 of the ultrasound system 100 of FIG. 1, includes an image display portion 902 having an ultrasound image 904. The ultrasound image 904 shown in FIG. 8 is a 2D SAX ultrasound image view of a left atrial appendage 930. The measurement processor 190 may be configured to provide various measurements 924, 926 of the orifice of the left atrial appendage 930 to assist with selection of an appropriate occlusion device for a left atrial appendage closure procedure (LAAC), for example. As an example, the measurement processor 190 may perform a length measurement 924, width measurement 926, circumference measurement, and/or any suitable measurement. The measurement processor 190 may be configured to present the measurement results at the display system 134. The measurement results may additionally and/or alternatively be stored at archive 138 and/or any suitable computer readable medium.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present 2D ultrasound images 304, 404, 504 and/or ultrasound slices 804, 904, 1004B, 1004C, 1004D extracted from 3D/4D volumes, rendered 3D/4D volumes 604, 704, 1004A, detected and tracked anatomical structure information 406, 408, 410, 506, 508, 510, 806, 808, 810, region of interest information 512, anatomical structure orientation information 614, 616, 714, 716, volume rendering viewing directions 820, volume rendering cropping planes 818, slice extraction planes 410, 510, 810, 822, measurements 924, 926, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores 2D ultrasound images 304, 404, 504 and/or ultrasound slices 804, 904, 1004B, 1004C, 1004D extracted from 3D/4D volumes, rendered 3D/4D volumes 604, 704, 1004A, detected and tracked anatomical structure information 406, 408, 410, 506, 508, 510, 806, 808, 810, region of interest information 512, anatomical structure orientation information 614, 616, 714, 716, volume rendering viewing directions 820, volume rendering cropping planes 818, slice extraction planes 410, 510, 810, 822, measurements 924, 926, instructions for automatically detecting and tracking the left atrial appendage and other anatomical structures, instructions for positioning regions of interest 512 surrounding the left atrial appendage and other anatomical structures, instructions for modifying region of interest positions and/or sizes, instructions for triggering a 3D/4D volume acquisition, instructions for estimating a current orientation of a left atrial appendage within ultrasound image data, instructions for calculating a rotation of a volume from an estimated current orientation to a pre-defined orientation, pre-defined orientations, instructions for rendering ultrasound volumes 604, 704, instructions for extracting ultrasound images slices 804, 904, 1004B, 1004C, 1004D from ultrasound volumes, and/or instructions for performing measurements 924, 926, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the structure detection processor 140 and/or orientation estimation processor 160. For example, the artificial intelligence model inferenced by the structure detection processor 140 may be trained to automatically identify anatomical structures depicted in an ultrasound image and/or volume using database(s) 220 of classified ultrasound images and/or volumes of anatomical structures (e.g., left atrial appendage). As another example, the artificial intelligence model inferenced by the orientation estimation processor 160 may be trained to automatically identify selected target structures (e.g., left atrial appendage), surrounding structures (e.g., pulmonary valves), target structure shapes, major/minor axes of target structures, and the like depicted in ultrasound image data using database(s) 220 of classified ultrasound images of possible target structures.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 10:
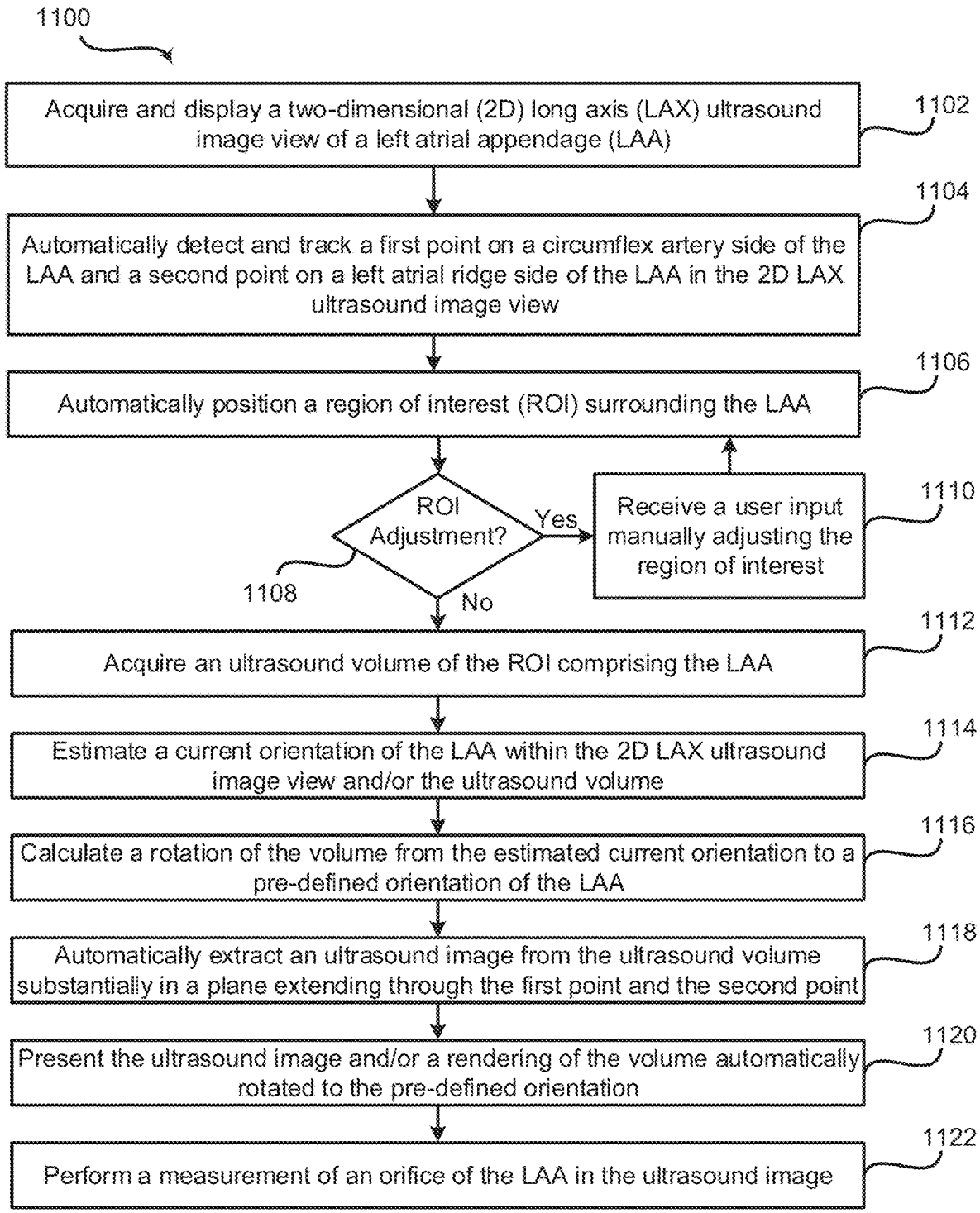
FIG. 10 is a flow chart illustrating exemplary steps that may be utilized for automatically acquiring an ultrasound volume to extract a two-dimensional (2D) short axis view of a left atrial appendage, in accordance with various embodiments.

FIG. 10 is a flow chart 1100 illustrating exemplary steps 1102-1122 that may be utilized for automatically acquiring an ultrasound volume 604, 704, 1004A to extract a two-dimensional (2D) short axis view 1004B of a left atrial appendage, in accordance with various embodiments. Referring to FIG. 10, there is shown a flow chart 1100 comprising exemplary steps 1102 through 1122. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 1102, an ultrasound system 100 acquires and displays a 2D LAX ultrasound image view 304, 404, 504, 804, 1004C of a left atrial appendage 330, 430, 530, 830. For example, an ultrasound probe 104 of the ultrasound system 100 may be operable to acquire 2D ultrasound images, ultrasound volumes, and/or any suitable ultrasound images. The acquired ultrasound images may be presented at the display system 134, provided to a structure detection processor 140 of a signal processor 132 of the ultrasound system 100, and/or stored at archive 138 and/or any suitable computer readable medium. In various embodiments, a single user input may initiate performance of steps 1104, 1106, and 1112-1122 of the process 1100.

At step 1104, a signal processor 132 of the ultrasound system 100 automatically detects and tracks a first point 406, 506, 806 on a circumflex artery side of the left atrial appendage 330, 430, 530, 830 and a second point 408, 508, 808 on the left atrial ridge side of the left atrial appendage 330, 430, 530, 830 in the 2D LAX ultrasound image view 304, 404, 504, 804, 1004C. For example, a structure detection processor 140 of the signal processor 132 may be configured to analyze acquired 2D LAX ultrasound images 304, 404, 504, 804, 1004C to detect a presence and location of the left atrial appendage 330, 430, 530, 830, including the first point 406, 506, 806 on the circumflex artery side and the second point 408, 508, 808 on the left atrial ridge side. The structure detection processor 140 may further be configured to identify a plane 410, 510, 810 passing through the first 406, 506, 806 and second 408, 508, 808 points of the left atrial appendage 330, 430, 530, 830. The structure detection processor 140 may include, for example, image analysis algorithms, one or more deep neural networks (e.g., a convolutional neural network such as u-net) and/or may utilize any suitable form of image analysis techniques, artificial intelligence, or machine learning processing functionality configured to detect and localize the left atrial appendage 330, 430, 530, 830 and associated anatomical structures in the 2D LAX ultrasound image views 304, 404, 504, 804, 1004C. The detected and localized left atrial appendage 330, 430, 530, 830, first point 406, 506, 806 on a circumflex artery side, second point 408, 508, 808 on the left atrial ridge side, and/or identified plane 410, 510, 810 may be provided by the structure detection processor 140 to a region of interest processor 150 and/or slice extraction processor 180 of the signal processor 132. Additionally and/or alternatively, the detected and localized left atrial appendage 330, 430, 530, 830, first point 406, 506, 806 on a circumflex artery side, second point 408, 508, 808 on the left atrial ridge side, and/or identified plane 410, 510, 810 may be stored at archive 138 and/or any suitable computer readable medium.

At step 1106, the signal processor 132 of the ultrasound system 100 automatically positions a region of interest 512 surrounding the left atrial appendage 330, 430, 530, 830. For example, a region of interest processor 150 of the signal processor 132 may be configured to position a region of interest 512 surrounding the left atrial appendage 330, 430, 530, 830 detected and localized by the structure detection processor 140. The region of interest processor 150 may be configured to receive from the structure detection processor 140, or retrieve from the archive 138 and/or any suitable data storage medium, the identity and location of the left atrial appendage 330, 430, 530, 830. In various embodiments, the region of interest processor 150 may be configured to identify the localized left atrial appendage 330, 430, 530, 830 at a display system 134 of the ultrasound system 100 by overlaying a bounding box, colorizing pixels, and/or any suitable identification technique.

At step 1108, the signal processor 132 of the ultrasound system 100 determines whether a modification to the region of interest 512 has been received from a user input device 130. In various embodiments, a region of interest 512 may not be displayed and/or may not be modifiable. In such embodiments, the process 1100 may skip steps 1108 and 1110.

At step 1110, the signal processor 132 of the ultrasound system 100 receives a modification to the region of interest 512. For example, the region of interest processor 150 may be configured to receive an instruction to modify the region of interest 512. As an example, in response to the region of interest processor 150 causing the display system 134 to present the 2D LAX ultrasound image view 504 with the region of interest 512 surrounding a left atrial appendage 530, an ultrasound operator may provide an input via the user input device 130 and/or touchscreen display 130, 134 to modify a size and/or location of the displayed region of interest 512. The process 1100 then returns to step 1106 for the region of interest processor 150 to cause the display system 134 to present the 2D LAX ultrasound image view 504 with the modified region of interest 512 surrounding the left atrial appendage 530. In various embodiments, a region of interest 512 may not be displayed and/or may not be modifiable. In such embodiments, the process 1100 may skip steps 1108 and 1110.

At step 1112, the signal processor 132 of the ultrasound system 100 may cause the ultrasound probe 104 to acquire an ultrasound volume 604, 704 of the region of interest (ROI) 512 comprising the left atrial appendage 530, 630, 730. For example, the region of interest processor 150 may be configured to initiate a 3D/4D volume acquisition of the region of interest 512 automatically and/or in response to a user input. As an example, the region of interest processor 150 may automatically initiate the ultrasound volume acquisition by the ultrasound probe 104 if the region of interest 512 is not modifiable and/or if a user input is not received to modify the position and/or size of the region of interest 512 in a predetermined period of time. As another example, the region of interest processor 150 may be configured to initiate the ultrasound volume acquisition by the ultrasound probe 104 in response to a user input. In addition, the region of interest processor 150 may be configured to initiate the ultrasound volume acquisition by the ultrasound probe 104 in response to a predetermined period of time expiring after the region of interest 512 has been modified and/or in response to a user input after the region of interest 512 has been modified. The acquired ultrasound volume 604, 704 may be provided to an orientation estimation processor 160 of the signal processor 132 and/or stored at archive 138 and/or any suitable computer readable medium.

At step 1114, the signal processor 132 of the ultrasound system 100 may estimate a current orientation of the left atrial appendage 630 within the 2D LAX ultrasound image 504 and/or the ultrasound volume 604. For example, an orientation estimation processor 160 of the signal processor 132 may be configured to estimate a current orientation of the left atrial appendage 630 within the 2D LAX ultrasound image 504 and/or the 3D/4D volume 604. As an example, the orientation estimation processor 160 may perform image segmentation and/or any suitable image identification techniques to estimate a current orientation of the left atrial appendage 630 depicted in the ultrasound image data. The orientation estimation processor 160 may be configured to segment and/or otherwise identify the left atrial appendage 630 within the ultrasound image data. In this regard, the orientation estimation processor 160 may include, for example, image analysis algorithms, artificial intelligence algorithms, one or more deep neural networks (e.g., a convolutional neural network such as u-net) and/or may utilize any suitable form of artificial intelligence image analysis techniques or machine learning processing functionality configured to provide segmentation of the left atrial appendage 630 and/or any suitable anatomical structure 640. The orientation estimation processor 160 may be configured to store the estimated current orientation information at archive 138 and/or any suitable storage medium. The orientation estimation processor 160 may be configured to provide a volume rotation processor 170 of the signal processor 132 with the estimated current orientation information. The estimated current orientation information may comprise, for example, location and boundaries of anatomical structures 630, 640, shape of anatomical structures 630, 640, major/minor axis information 614, 616, and the like.

At step 1116, the signal processor 132 of the ultrasound system 100 may calculate a rotation of the ultrasound volume from the estimated current orientation 604 to a pre-defined orientation 704 of the left atrial appendage 630, 730. For example, a volume rotation processor 170 of the signal processor 132 may be configured to rotate the ultrasound volume 604 to a pre-defined orientation 704. As an example, the volume rotation 170 processor may configured to rotate the ultrasound volume 604 based on the estimated current orientation information from the orientation estimation processor 160 and a pre-defined orientation. The pre-defined orientation may correspond with a standard orientation from echocardiography guidelines and/or any suitable pre-defined orientations from other guidelines, settings, and/or configurations. The volume rotation processor 170 may, for example, calculate a rotation angle and rotation amount to transform the volume from the estimated current orientation 604 to the pre-defined orientation 704. The volume rotation processor 170 may reference the major axis 614 and/or minor axis 616 of the shape of the left atrial appendage 630 and the location information for the surrounding structure 640 in the estimated current orientation information with reference to the pre-defined orientation information to calculate and provide the rotation amount and rotation angle to transform the ultrasound volume 604 to the pre-defined orientation 704.

At step 1118, the signal processor 132 of the ultrasound system 100 may automatically extract an ultrasound image 904, 1004B from the ultrasound volume 604, 704 substantially in a plane 410, 510, 810 extending through the first point 406, 506, 806 and the second point 408, 508, 808. For example, the structure detection processor 140 may be configured to detect and track the first point 406, 506, 806 on the circumflex artery side of the left atrial appendage 430, 530, 630, 730, 830 and the second point 408, 508, 808 on the left atrial ridge side of the left atrial appendage 430, 530, 630, 730, 830 in the acquired ultrasound volume 604, 704. The structure detection processor 140 may be configured to identify a plane 410, 510, 810 extending through the first point 406, 506, 806 and second point 408, 508, 808. A slice extraction processor 180 of the signal processor 132 may be configured to receive from the structure detection processor 140 or retrieve from archive 138 and/or any suitable data storage medium the locations of the first point 406, 506, 806, second point 408, 508, 808, and/or plane 410, 510, 810 identified by the structure detection processor 140. The slice extraction processor 180 may be configured to automatically extract an ultrasound image 904, 1004B substantially in the plane 410, 510, 810, which corresponds with a 2D SAX ultrasound image view 904, 1004B of the left atrial appendage 930, based on the first point 406, 506, 806, second point 408, 508, 808, and/or plane 410, 510, 810 identified by the structure detection processor 140. For purposes of the present application, an ultrasound image 904, 1004B "substantially" in the plane 410, 510, 810 refers to an ultrasound image of the plane 410, 510, 810 extending between the first 406, 506, 806 and second 408, 508, 808 points and/or an ultrasound image in planes parallel to plane 410, 510, 810 up to 1 centimeter into the left atrial appendage 430, 530, 630, 730, 830. In various embodiments, the slice extraction processor 180 is configured to extract additional planes 822, 1004D selected by an ultrasound operator. For example, an ultrasound operator may position additional planes 822 in the 2D LAX ultrasound view 304, 404, 504, 804, 1004C and the slice extraction processor 180 may be configured to extract the additional planes 822, 1004D corresponding with the locations selected by the ultrasound operator in the 2D LAX ultrasound view 304, 404, 504, 804, 1004C.

At step 1120, the signal processor 132 of the ultrasound system 100 may cause the display system 134 to present the ultrasound image 904, 1004B and/or a rendering of the volume 604, 704, 1004A automatically rotated to the pre-defined orientation 704. For example, the slice extraction processor 180 of the signal processor 132 may be configured to cause a display system 134 to present the ultrasound image 904, 1004B and/or additional ultrasound images 822, 1004D extracted from the ultrasound volume 604, 704 at step 1118. As another example, the volume rotation processor 170 may be configured to render and cause a display system 134 to present the rotated and rendered ultrasound volume 704, 1004A.

At step 1122, the signal processor 132 of the ultrasound system 100 may perform a measurement 924, 926 of an orifice of the left atrial appendage 930 in the ultrasound image 904. For example, a measurement processor 190 of the signal processor 132 may be configured to perform circumference measurements, length measurements 924, width measurements 926, and/or any suitable measurements on the left atrial appendage orifice 930 depicted in the 2D SAX ultrasound view 904, 1004B. The measurement processor 190 may be configured to cause the display system 134 to present the measurement(s) 924, 926. The measurement processor 190 may be configured to store the measurement(s) 924, 926 at archive 138 and/or any suitable data storage medium.

In a preferred embodiment, after the 2D LAX ultrasound image view 304, 404, 504, 804, 1004C of the left atrial appendage 330, 430, 530, 830 is acquired and displayed at step 1102, a user may provide a single user input to automatically navigate from the 2D LAX ultrasound image view 304, 404, 504, 804, 1004C to a 2D SAX ultrasound image view 904, 1004B and optionally automatically perform at least one measurement 924, 926 of an orifice area of a left atrial appendage 930. In other words, steps 1108 and 1110 of the process 1100 are omitted, and steps 1104, 1106 and 1112-1122 are performed in response to a single user input (i.e., without any other human intervention). In various embodiments, navigating from the 2D LAX ultrasound image view 304, 404, 504, 804, 1004C to the 2D SAX ultrasound image view 904, 1004B and automatically performing at least one measurement 924, 926 of an orifice area of a left atrial appendage 930 occurs substantially in real-time (i.e., in less than 10 seconds), which may save 2-3 minutes corresponding with the typical time it takes to manually navigate to the 2D SAX view from the 2D LAX view.

Aspects of the present disclosure provide a method 1100 and system 100 for automatically acquiring an ultrasound volume 604, 704 to extract a two-dimensional (2D) short axis view 904, 1004B of a left atrial appendage. In accordance with various embodiments, the method 1100 may comprise acquiring 1102, by an ultrasound probe 104 of an ultrasound system 100, a two-dimensional long axis ultrasound image view 304, 404, 504, 804, 1004C of a left atrial appendage 330, 430, 530, 830. The method 1100 may comprise automatically detecting 1104, by at least one processor 132, 140 of the ultrasound system 100, a first point 406, 506, 806 on a circumflex artery side of the left atrial appendage 330, 430, 530, 830 and a second point 408, 508, 808 on a left atrial ridge side of the left atrial appendage 330, 430, 530, 830 in the two-dimensional long axis ultrasound image view 304, 404, 504, 804, 1004C. The method 1100 may comprise acquiring 1112, by the ultrasound probe 104, an ultrasound volume 604, 704 comprising the left atrial appendage 630, 730. The method 1100 may comprise automatically extracting 1118 from the ultrasound volume 604, 704, by the at least one processor 132, 180, an ultrasound image 904, 1004B substantially in a plane 410, 510, 810 extending through the first point 406, 506, 806 and the second point 408, 508, 808. The method 1100 may comprise causing 1120, by the at least one processor 132, 180, a display system 134 to present the ultrasound image 904, 1004B.

In an exemplary embodiment, the ultrasound image 904, 1004B corresponds with a two-dimensional short axis ultrasound image view 904, 1004B of a left atrial appendage 930. In a representative embodiment, the method 1100 comprises estimating 1114, by the at least one processor 132, 160, a current orientation of the left atrial appendage 630. The method 1100 may comprise calculating 1116, by the at least one processor 132, 170, a rotation of the ultrasound volume from the estimated current orientation 604 to a pre-defined orientation 704 of the left atrial appendage 630, 730. The method 1100 may comprise causing 1120, by the at least one processor 132, 170, the display system 134 to present a rendering of the ultrasound volume 704 automatically rotated to the pre-defined orientation. In various embodiments, the rendering of the ultrasound volume 704 automatically rotated to the pre-defined orientation corresponds with a cropped plane 818 above the left atrial appendage 830 and parallel to the plane 810 extending through the first point 806 and the second point 808. A viewing angle 820 of the rendering of the ultrasound volume 704 automatically rotated to the pre-defined orientation may be perpendicular to the cropped plane 818. In certain embodiments, the method 1100 comprises automatically extracting 1118 from the ultrasound volume 604, 704, by the at least one processor 132, 180, an additional ultrasound image 1004D in an additional plane 822 perpendicular to the plane 410, 510, 810 and extending between the first point 806 and the second point 808. The method 1100 may comprise causing 1120, by the at least one processor 132, 180, the display system 134 to present the additional ultrasound image 1004D. In an exemplary embodiment, the method 1100 comprises automatically positioning 1106, by the at least one processor 132, 150, a region of interest 512 surrounding the left atrial appendage 330, 430, 530, 830 in the two-dimensional long axis ultrasound image view 304, 404, 504, 804, 1004C. The acquiring 1112 the ultrasound volume 604, 704 may correspond with the region of interest 512. In a representative embodiment, the method 1100 comprises receiving 1108, 1110, by the at least one processor 132, 150, a user input to modify the region of interest 512. The region of interest 512 may be presented at the display system 134. In various embodiments, the acquiring 1112 the ultrasound volume 604, 704 is automatically performed in response to not receiving a user input to modify the region of interest 512 presented at the display system 134 within a predetermined period of time. In certain embodiments, the method 1100 comprises performing 1122, by the at least one processor 132, 190, a measurement 924, 926 of an orifice of the left atrial appendage 930 in the ultrasound image 904. The measurement 924, 926 may comprise a circumference measurement of the orifice 930, a length measurement 924 of the orifice 930, and/or a width measurement 926 of the orifice 930.

Various embodiments provide a system 100 for automatically acquiring an ultrasound volume 604, 704 to extract a two-dimensional (2D) short axis view 904, 1004B of a left atrial appendage. The system 100 may comprise an ultrasound probe 104, at least one processor 132, 140, 150, 160, 170, 180, 190 and a display system 134. The ultrasound probe 104 may be configured to acquire a two-dimensional long axis ultrasound image view 304, 404, 504, 804, 1004C of a left atrial appendage 330, 430, 530, 830. The ultrasound probe 104 may be configured to acquire an ultrasound volume 604, 704 comprising the left atrial appendage 630, 730. The at least one processor 132, 140 may be configured to automatically detect a first point 406, 506, 806 on a circumflex artery side of the left atrial appendage 330, 430, 530, 830 and a second point 408, 508, 808 on a left atrial ridge side of the left atrial appendage 330, 430, 530, 830 in the two-dimensional long axis ultrasound image view 304, 404, 504, 804, 1004C. The at least one processor 132, 180 may be configured to automatically extract from the ultrasound volume 604, 704 an ultrasound image 904, 1004B substantially in a plane 410, 510, 810 extending through the first point 406, 506, 806 and the second point 408, 508, 808. The display system 134 may be configured to present the ultrasound image 904, 1004B.

In a representative embodiment, the ultrasound image 904, 1004B corresponds with a two-dimensional short axis ultrasound image view 904, 1004B of a left atrial appendage 930. In various embodiments, the at least one processor 132, 160 is configured to estimate a current orientation 604 of the left atrial appendage 630. The at least one processor 132, 170 may be configured to calculate a rotation of the ultrasound volume from the estimated current orientation 604 to a pre-defined orientation 704 of the left atrial appendage 730. The display system 134 may be configured to present a rendering of the ultrasound volume 604, 704, 1004A automatically rotated to the pre-defined orientation 704. In certain embodiments, the rendering of the ultrasound volume 604, 704, 1004A automatically rotated to the pre-defined orientation 704 corresponds with a cropped plane 818 above the left atrial appendage 830 and parallel to the plane 810 extending through the first point 806 and the second point 808. A viewing angle 820 of the rendering of the ultrasound volume 604, 704, 1004A automatically rotated to the pre-defined orientation 704 may be perpendicular to the cropped plane 818. In an exemplary embodiment, the at least one processor 132, 180 is configured to automatically extract, from the ultrasound volume 604, 704, an additional ultrasound image 1004D in an additional plane 822 perpendicular to the plane 410, 510, 810 and extending between the first point 806 and the second point 808. The display system 134 may be configured to present the additional ultrasound image 1004D. In a representative embodiment, the at least one processor 132, 150 is configured to automatically position a region of interest 512 surrounding the left atrial appendage 530 in the two-dimensional long axis ultrasound image view 504. The ultrasound probe 104 may be operable to acquire the ultrasound volume 604, 704 based on the region of interest 512. In various embodiments, the region of interest 512 is presented at the display system 134. The at least one processor 132, 150 may be configured to receive a user input to modify the region of interest 512 presented at the display system 134. In an exemplary embodiment, the at least one processor 132, 190 is configured to perform a measurement 924, 926 of an orifice of the left atrial appendage 930 in the ultrasound image 904, 1004B. The measurement may comprise a circumference measurement of the orifice 930, a length measurement 924 of the orifice 930, and/or a width measurement 926 of the orifice 930.

Certain embodiments provide a system 100 for automatically acquiring an ultrasound volume 604, 704 to extract a two-dimensional (2D) short axis view 904, 1004B of a left atrial appendage. The system 100 may comprise an ultrasound probe 104, at least one processor 132, 140, 150, 160, 170, 180, 190 and a display system 134. The ultrasound probe 104 may be configured to acquire a two-dimensional long axis ultrasound image view 304, 404, 504, 804, 1004C of a left atrial appendage 330, 430, 530, 830. The ultrasound probe 104 may be configured to acquire an ultrasound volume 604, 704 comprising the left atrial appendage 630, 730. The at least one processor 132, 140 may be configured to automatically detect a first point 406, 506, 806 on a circumflex artery side of the left atrial appendage 330, 430, 530, 830 and a second point 408, 508, 808 on a left atrial ridge side of the left atrial appendage 330, 430, 530, 830 in the two-dimensional long axis ultrasound image view 304, 404, 504, 804. The at least one processor 132, 160 may be configured to estimate a current orientation 604 of the left atrial appendage 630. The at least one processor 132, 170 may be configured to calculate a rotation of the ultrasound volume from the estimated current orientation 604 to a pre-defined orientation 704 of the left atrial appendage 630, 730. The at least one processor 132, 180 may be configured to automatically extract, from the ultrasound volume 604, 704, an ultrasound image 904, 1004B substantially in a plane 410, 510, 810 extending through the first point 406, 506, 806 and the second point 408, 508, 808. The ultrasound image 904, 1004B may correspond with a two-dimensional short axis ultrasound image view 904, 1004B of a left atrial appendage 930. The display system 134 may be configured to present the ultrasound image 904, 1004B and a rendering of the ultrasound volume 604, 704, 1004A automatically rotated to the pre-defined orientation 704.

In various embodiments, the rendering of the ultrasound volume 604, 704, 1004A automatically rotated to the pre-defined orientation 704 corresponds with a cropped plane 818 above the left atrial appendage 830 and parallel to the plane 810 extending through the first point 806 and the second point 808. A viewing angle 820 of the rendering of the ultrasound volume 604, 704, 1004A automatically rotated to the pre-defined orientation 704 may be perpendicular to the cropped plane 818. In certain embodiments, the at least one processor 132, 180 is configured to automatically extract, from the ultrasound volume 604, 704, an additional ultrasound image 1004D in an additional plane 822 perpendicular to the plane 410, 510, 810 and extending between the first point 806 and the second point 808. The display system 134 may be configured to present the additional ultrasound image 1004D.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically acquiring an ultrasound volume to extract a two-dimensional (2D) short axis view of a left atrial appendage.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
acquiring, by an ultrasound probe of an ultrasound system, a two-dimensional long axis ultrasound image view of a left atrial appendage;
automatically detecting, by at least one processor of the ultrasound system, a first point on a circumflex artery side of the left atrial appendage and a second point on a left atrial ridge side of the left atrial appendage in the two-dimensional long axis ultrasound image view;
acquiring, by the ultrasound probe, an ultrasound volume comprising the left atrial appendage;
automatically extracting from the ultrasound volume, by the at least one processor, an ultrasound image substantially in a plane extending through the first point and the second point; and
causing, by the at least one processor, a display system to present the ultrasound image.

2. The method of claim 1, wherein the ultrasound image corresponds with a two-dimensional short axis ultrasound image view of a left atrial appendage.

3. The method of claim 1, further comprising:
estimating, by the at least one processor, a current orientation of the left atrial appendage;
calculating, by the at least one processor, a rotation of the ultrasound volume from the estimated current orientation to a pre-defined orientation of the left atrial appendage; and
causing, by the at least one processor, the display system to present a rendering of the ultrasound volume automatically rotated to the pre-defined orientation.

4. The method of claim 3, wherein the rendering of the ultrasound volume rotated to the pre-defined orientation corresponds with a cropped plane above the left atrial appendage and parallel to the plane extending through the first point and the second point, and wherein a viewing angle of the rendering of the ultrasound volume rotated to the pre-defined orientation is perpendicular to the cropped plane.

5. The method of claim 1, further comprising:
automatically extracting from the ultrasound volume, by the at least one processor, an additional ultrasound image in an additional plane perpendicular to the plane and extending between the first point and the second point; and
causing, by the at least one processor, the display system to present the additional ultrasound image.

6. The method of claim 1, comprising automatically positioning, by the at least one processor, a region of interest surrounding the left atrial appendage in the two-dimensional long axis ultrasound image view, wherein the acquiring the ultrasound volume corresponds with the region of interest.

7. The method of claim 6, comprising receiving, by the at least one processor, a user input to modify the region of interest, wherein the region of interest is presented at the display system.

8. The method of claim 7, wherein the acquiring the ultrasound volume is automatically performed in response to not receiving a user input to modify the region of interest presented at the display system within a predetermined period of time.

9. The method of claim 1, comprising performing, by the at least one processor, a measurement of an orifice of the left atrial appendage in the ultrasound image, wherein the measurement comprises:
- a circumference measurement of the orifice,
- a length measurement of the orifice, and/or
- a width measurement of the orifice.

10. An ultrasound system comprising:
an ultrasound probe configured to:
- acquire a two-dimensional long axis ultrasound image view of a left atrial appendage; and
- acquire an ultrasound volume comprising the left atrial appendage;

at least one processor configured to:
- automatically detect a first point on a circumflex artery side of the left atrial appendage and a second point on a left atrial ridge side of the left atrial appendage in the two-dimensional long axis ultrasound image view; and
- automatically extract from the ultrasound volume an ultrasound image substantially in a plane extending through the first point and the second point; and a display system configured to present the ultrasound image.

11. The ultrasound system of claim 10, wherein the ultrasound image corresponds with a two-dimensional short axis ultrasound image view of a left atrial appendage.

12. The ultrasound system of claim 10, wherein:
the at least one processor is configured to:
- estimate a current orientation of the left atrial appendage; and
- calculate a rotation of the ultrasound volume from the estimated current orientation to a pre-defined orientation of the left atrial appendage; and the display system is configured to present a rendering of the ultrasound volume automatically rotated to the pre-defined orientation.

13. The ultrasound system of claim 12, wherein the rendering of the ultrasound volume rotated to the pre-defined orientation corresponds with a cropped plane above the left atrial appendage and parallel to the plane extending through the first point and the second point, and wherein a viewing angle of the rendering of the ultrasound volume rotated to the pre-defined orientation is perpendicular to the cropped plane.

14. The ultrasound system of claim 10, wherein:
the at least one processor is configured to automatically extract, from the ultrasound volume, an additional ultrasound image in an additional plane perpendicular to the plane and extending between the first point and the second point; and
the display system is configured to present the additional ultrasound image.

15. The ultrasound system of claim 10, wherein:
the at least one processor is configured to automatically position a region of interest surrounding the left atrial appendage in the two-dimensional long axis ultrasound image view, and
the ultrasound probe is operable to acquire the ultrasound volume based on the region of interest.

16. The ultrasound system of claim 15, wherein:
the region of interest is presented at the display system, and
the at least one processor is configured to receive a user input to modify the region of interest presented at the display system.

17. The ultrasound system of claim 10, wherein:
the at least one processor is configured to perform a measurement of an orifice of the left atrial appendage in the ultrasound image, and
the measurement comprises:
- a circumference measurement of the orifice,
- a length measurement of the orifice, and/or
- a width measurement of the orifice.

18. An ultrasound system comprising:
an ultrasound probe configured to:
- acquire a two-dimensional long axis ultrasound image view of a left atrial appendage; and
- acquire an ultrasound volume comprising the left atrial appendage;

at least one processor configured to:
- automatically detect a first point on a circumflex artery side of the left atrial appendage and a second point on a left atrial ridge side of the left atrial appendage in the two-dimensional long axis ultrasound image view;
- estimate a current orientation of the left atrial appendage;
- calculate a rotation of the ultrasound volume from the estimated current orientation to a pre-defined orientation of the left atrial appendage; and
- automatically extract, from the ultrasound volume, an ultrasound image substantially in a plane extending through the first point and the second point, wherein the ultrasound image corresponds with a two-dimensional short axis ultrasound image view of a left atrial appendage; and a display system configured to present:
- the ultrasound image; and
- a rendering of the ultrasound volume automatically rotated to the pre-defined orientation.

19. The ultrasound system of claim 18, wherein:
the rendering of the ultrasound volume rotated to the pre-defined orientation corresponds with a cropped plane above the left atrial appendage and parallel to the plane extending through the first point and the second point, and
a viewing angle of the rendering of the ultrasound volume rotated to the pre-defined orientation is perpendicular to the cropped plane.

20. The ultrasound system of claim 18, wherein:
the at least one processor is configured to automatically extract, from the ultrasound volume, an additional ultrasound image in an additional plane perpendicular to the plane and extending between the first point and the second point; and
the display system is configured to present the additional ultrasound image.

* * * * *